United States Patent
Hashiba et al.

[11] Patent Number: 5,786,479
[45] Date of Patent: Jul. 28, 1998

[54] PROCESS FOR PRODUCING A 6-SUBSITITUTED 2(1H)-QUINOXALINONE

[75] Inventors: Isao Hashiba, Funabashi; Masataka Hatanaka, Onoda, both of Japan

[73] Assignee: Nissan Chemical Industries, Ltd., Tokyo, Japan

[21] Appl. No.: 687,439

[22] PCT Filed: Feb. 8, 1995

[86] PCT No.: PCT/JP95/00173

§ 371 Date: Aug. 13, 1996

§ 102(e) Date: Aug. 13, 1996

[87] PCT Pub. No.: WO95/22531

PCT Pub. Date: Aug. 24, 1995

[30] Foreign Application Priority Data

Feb. 17, 1994 [JP] Japan ................................. 6-020296
Jan. 6, 1995 [JP] Japan ................................. 7-000548

[51] Int. Cl.$^6$ ........................................ C07D 241/36
[52] U.S. Cl. ................................................ 544/354
[58] Field of Search ................................... 544/354

[56] References Cited

FOREIGN PATENT DOCUMENTS 0295797  5/1988  European Pat. Off. .

OTHER PUBLICATIONS

Chemical Abstracts, vol. 104, No. 28, pp. 665–666, JP 60 158 184, 1986; Aug. 19, 1985.
Chemical Abstracts, vol. 98, No. 98, p. 661, 1983, JP 57 197 270, Dec. 3, 1982.

Primary Examiner—Matthew V. Grumbling
Assistant Examiner—Michael Bucknum
Attorney, Agent, or Firm—Oblon, Spivak, McClelland, Maier & Neustadt, P.C.

[57] ABSTRACT

A process for producing a 6-substituted 2(1H)-quinoxalinone of the formula (I):

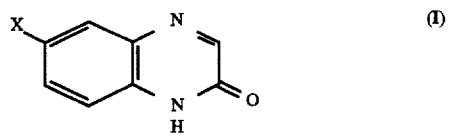

wherein X is a halogen atom, a trihalogeno-substituted $C_{1-5}$ alkyl group or a nitro group, which comprises reacting a 6-substituted 2(1H)-quinoxalinone-N-oxide of the formula (II):

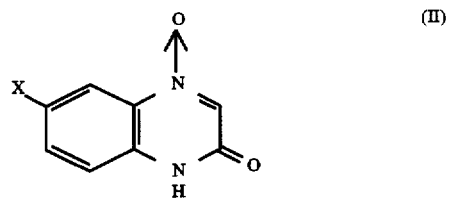

wherein X is as defined above, with an alkali metal hydrosulfide and/or an alkali metal sulfide in the presence of from 1 to 20 mol times of an alkali.

15 Claims, No Drawings

PROCESS FOR PRODUCING A 6-SUBSTITUTED 2(1H)-QUINOXALINONE

TECHNICAL FIELD

The present invention relates to a process for producing a 6-substituted 2(1H)-quinoxalinone.

The 6-substituted 2(1H)-quinoxalinone is useful as an intermediate for an excellent herbicide, as disclosed in Japanese Examined Patent Publication No. 33389/1985.

BACKGROUND ART

As a method for producing a 6-substituted 2(1H)-quinoxalinone, it is common to produce it by reducing the corresponding 6-substituted 2(1H)-quinoxalinone-N-oxide.

A reagent reduction method wherein zinc metal, sodium borohydride, a sulfite compound or the like is used as a reducing agent, or a hydrogen reduction method wherein a palladium catalyst, a platinum catalyst, a Raney nickel catalyst or the like is used, has been known.

In the hydrogen reduction method wherein a catalyst is used, a reaction for removal of the substituent may occur depending upon the type of the substituent of the 6-substituted 2(1H)-quinoxalinone. As such a substituent, a halogen atom or the like may, for example, be mentioned.

To prevent such a reaction for removal of the substituent, a method has been developed wherein hydrogen reduction is carried out in the presence of a palladium catalyst, a platinum catalyst, a Raney nickel catalyst or the like which is poisoned with a sulfur compound.

In the reagent reduction method, the yield is poor with a reduction method wherein zinc metal is used.

With a reduction method wherein sodium borohydride is used, the yield is high, and the reaction operation is relatively easy, but in addition to a drawback that the cost is high, it may often happens that a reduced product having the reaction proceeded excessively is produced as a by-product.

A reduction method wherein a sulfite compound is used, is inexpensive, but a 2,3-dihydroxyquinoxaline compound will be produced as a by-product, whereby the yield will be poor.

For the method wherein hydrogen reduction is carried out in the presence of a palladium catalyst, a platinum catalyst or a Raney nickel catalyst poisoned with a sulfur compound, a high level of technique is required for the preparation of the catalyst, and it may often happen that the reduction rate decreases, or the reaction for removal of the substituent will not be suppressed.

Further, hydrogen reduction of a slurry system having an alkali salt of the 6-substituted 2(1H)-quinoxalinone-N-oxide precipitated, by means of the above catalyst, is difficult, and in order to let the hydrogen reduction proceed, it is necessary to dissolve the alkali salt of the 6-substituted 2(1H)-quinoxalinone-N-oxide.

DISCLOSURE OF THE INVENTION

The present inventors have made an extensive study to overcome the drawbacks of the above reduction reaction and as a result, have found that the conversion and selectivity can be improved to a large extent by a reduction reaction wherein an inexpensive alkali metal hydrosulfide and/or alkali metal sulfide is used. The present invention has been accomplished on the basis of this discovery.

Namely, the present invention provides a process for producing a 6-substituted 2(1H)-quinoxalinone of the formula (I):

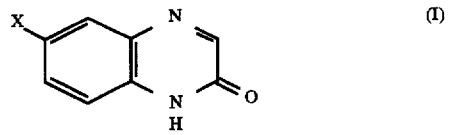

wherein X is a halogen atom, a trihalogeno-substituted $C_{1-5}$ alkyl group or a nitro group, which comprises reacting a 6-substituted 2(1H)-quinoxalinone-N-oxide of the formula (II):

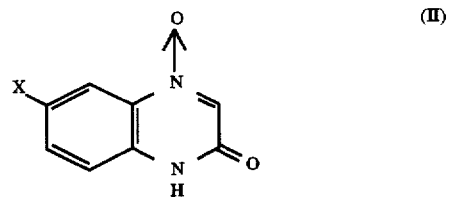

wherein X is a halogen atom, a trihalogeno-substituted $C_{1-5}$ alkyl group or a nitro group, with an alkali metal hydrosulfide and/or an alkali metal sulfide in the presence of from 1 to 20 mol times of an alkali;

the process for producing a 6-substituted 2(1H)-quinoxalinone of the formula (I), wherein after reacting the 6-substituted 2(1H)-quinoxalinone-N-oxide of the formula (II) with an alkali metal hydrosulfide and/or an alkali metal sulfide in the presence of from 1 to 20 mol times of an alkali, the reaction product is added to and treated with an acid of from 80° to 100° C.;

the process for producing a 6-substituted 2(1H)-quinoxalinone of the formula (I), wherein a 4-halogeno-2-nitroacetoacetoanilide of the formula (III):

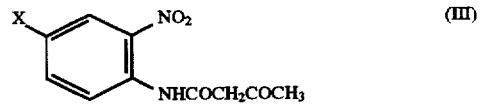

is reacted in the presence of from 3 to 20 mol times of an alkali to obtain a reaction mixture containing an alkali salt of the 6-substituted 2(1H)-quinoxalinone-N-oxide of the formula (II), and then the reaction mixture and an alkali metal hydrosulfide and/or an alkali metal sulfide are reacted; and the process for producing a 6-substituted 2(1H)-quinoxalinone of the formula (I), wherein the 4-halogeno-2-nitroacetoacetoanilide of the formula (III) is reacted in the presence of from 3 to 20 mol times of an alkali to obtain a reaction mixture containing an alkali salt of the 6-substituted 2(1H)-quinoxalinone-N-oxide of the formula (II), thereafter the reaction mixture and an alkali metal hydrosulfide and/or an alkali metal sulfide are reacted, and then the reaction product is added to and treated with an acid of from 80° to 100° C.

In the above formulas, X may, for example, be a halogen atom, a trihalogeno $C_{1-5}$ alkyl group or a nitro group.

The halogen atom may, for example, be a fluorine atom, a chlorine atom, a bromine atom or an iodine atom.

The trihalogeno-substituted $C_{1-5}$ alkyl group may, for example, be a trifluoromethyl group, a trifluoro-n-butyl group, a trichloromethyl group, a trichloro-n-propyl group, a tribromomethyl group, a tribromo-n-butyl group, tri-iodomethyl group or a triiodo-i-propyl group.

The method for preparing the 6-substitued 2(1H)-quinoxalinone-N-oxide of the formula (II) will be described below.

The 6-substitued 2(1H)-quinoxalinone-N-oxide of the present invention can be produced from a 4-halogeno-2-nitroacetoacetoanilide of the formula (III) and an alkali.

The alkali may, for example, be lithium hydroxide, sodium hydroxide or potassium hydroxide, and it may be used as it is, or in the form of e.g. an aqueous alkaline solution.

The amount of the alkali to be used, is usually within a range of from 3 to 20 mol times, preferably within a range of from 3 to 5 mol times, relative to the 4-halogeno-2-nitroacetoacetoanilide of the formula (III).

If sodium hydroxide is used as the alkali, the resulting sodium salt of the 6-substitued 2(1H)-quinoxalinone-N-oxide of the formula (II) will precipitate, and the reaction mixture will be a slurry.

Whereas, if potassium hydroxide is used as the alkali, the resulting potassium salt of the 6-substituted 2(1H)-quinoxalinone-N-oxide of the formula (II) will not precipitate, and the reaction mixture will be a uniform solution, whereby the reaction operation or the like will be simplified. However, potassium hydroxide is expensive as compared with sodium hydroxide, and the yield of the 6-substituted 2(1H)-quinoxalinone-N-oxide of the formula (II) tends to be lower by a few %.

For this step, not only water, but also an organic solvent may be used as the case requires.

The organic solvent may, for example, be toluene, diethyl ether, tetrahydrofuran, 1,4-dioxane, ethylene glycol diethyl ether, diethylene glycol diethyl ether or dimethylimidazolidinone. Such solvents may be used in combination.

When water and an organic solvent are used in combination, the yields of the 6-substitued 2(1H)-quinoxalinone-N-oxide of the formula (II) and its alkali salt can be improved.

The reaction temperature is usually within a range of from 0° to 100° C., preferably within a range of from 50° to 80° C.

By subjecting the reaction mixture of the formed alkali salt of the 6-substituted 2(1H)-quinoxalinone-N-oxide of the formula (II) to acid treatment, it is possible to produce the 6-substitued 2(1H)-quinoxalinone-N-oxide of the formula (II).

The acid may, for example, be a mineral acid such as hydrochloric acid, sulfuric acid or nitric acid, or an organic acid such as p-toluenesulfonic acid, and it may be used by itself or in the form of an aqueous acid solution.

The amount of the acid to be used, is an amount whereby the reaction mixture becomes acidic.

The temperature for the acid treatment is usually within a range of from 0° to 100° C., preferably within a range of from 0° to 40° C.

Now, the reduction reaction of the obtained 6-substitued 2(1H)-quinoxalinone-N-oxide of the formula (II) with an alkali metal hydrosulfide and/or an alkali metal sulfide will be described below.

The amount of the alkali to be used, is usually within a range of from 1 to 20 mol times, preferably within a range of from 1 to 2 mol times, relative to the 6-substituted 2(1H)-quinoxalinone-N-oxide of the formula (II).

If the amount of sodium hydroxide exceeds the range of 3.0 mol times relative to the 6-substituted 2(1H)-quinoxalinone-N-oxide of the formula (II), a sodium salt of the 6-substituted 2(1H)-quinoxalinone-N-oxide will precipitate, and the reaction system will be a slurry.

If the amount of sodium hydroxide to be used, is within a range of from 1 to 3.0 mol times relative to the 6-substituted 2(1H)-quinoxalinone-N-oxide of the formula (II), a sodium salt of the 6-substituted 2(1H)-quinoxalinone-N-oxide of the formula (II) will not precipitate, and the reaction system becomes a uniform solution.

Whereas, if potassium hydroxide is used as the alkali, the resulting potassium salt of the 6-substituted 2(1H)-quinoxalinone-N-oxide of the formula (II) will not precipitate, and the reaction system becomes a uniform solution, whereby the reaction operation or the like will be simplified. However, potassium hydroxide is expensive as compared with sodium hydroxide, and the yield of the 6-substituted 2(1H)-quinoxalinone of the formula (I) tends to be lower by a few %.

Namely, the amount of the alkali to be used in a case where the 6-substituted 2(1H)-quinoxalinone-N-oxide of the formula (II) is used as the starting material, is usually within a range of from 1 to 3.0 mol times relative to the 6-substituted 2(1H)-quinoxalinone-N-oxide of the formula (II).

Further, the reaction mixture containing the alkali salt of the 6-substituted 2(1H)-quinoxalinone-N-oxide of the formula (II) formed from the above-mentioned 4-halogeno-2-nitroacetoacetoanilide of the formula (III), may be directly subjected to the reduction reaction with an alkali metal hydrosulfide and/or an alkali metal sulfide.

When the reaction mixture containing the alkali salt of the 6-substituted 2(1H)-quinoxalinone-N-oxide of the formula (II) formed from the 4-halogeno-2-nitroacetoacetoanilide of the formula (III) is subjected to the reduction reaction with an alkali metal hydrosulfide and/or an alkali metal sulfide, it is not necessary to add an alkali afresh.

Otherwise, the alkali salt of the 6-substituted 2(1H)-quinoxalinone-N-oxide of the formula (II) formed from the 4-halogeno-2-nitroacetoacetoanilide of the formula (III) may be separated by filtration and then subjected to the reduction reaction by an alkali metal hydrosulfide and/or an alkali metal sulfide.

The alkali metal hydrosulfide may, for example, be sodium hydrosulfide or potassium hydrosulfide.

The alkali metal sulfide may, for example, be sodium sulfide or potassium sulfide.

The alkali metal hydrosulfide and the alkali metal sulfide may be used alone, respectively, or may be used in combination as a mixture.

The amount of the alkali metal hydrosulfide and/or the alkali metal sulfide to be used, is usually within a range of from 1.0 to 20 mol times, preferably within a range of from 1.5 to 3 mol times, relative to the 6-substituted 2(1H)-quinoxalinone-N-oxide of the formula (II).

The alkali metal hydrosulfide and/or the alkali metal sulfide may be used as it is in a solid state or may be used in the form of an aqueous solution.

The reduction reaction by the alkali metal hydrosulfide and/or the alkali metal sulfide may be carried out under atmospheric pressure or under elevated pressure.

The temperature for the reduction reaction by the alkali metal hydrosulfide and/or the alkali metal sulfide, is usually within a range of from 0° to 200° C., preferably within a range of from 40° to 100° C.

For this reduction reaction, not only water, but also an organic solvent may be used, as the case requires.

The organic solvent may, for example, be toluene, diethyl ether, tetrahydrofuran, 1,4-dioxane, ethylene glycol diethyl ether, diethylene glycol diethyl ether or dimethylimidazolidinone. These solvents may be used in combination.

The reduction reaction by the alkali metal hydrosulfide and/or the alkali metal sulfide is highly economical, since the reducing agent is inexpensive, and the conversion and selectivity can be improved to a large extent without excessive proceeding of the reduction reaction of the 6-substituted 2(1H)-quinoxalinone-N-oxide of the formula (II).

Further, a characteristic of the reduction reaction by the alkali metal hydrosulfide and/or the alkali metal sulfide according to the present invention, is that the reduction reaction proceeds smoothly even when applied to a slurry system having the alkali salt of the 6-substituted 2(1H)-quinoxalinone-N-oxide of the formula (II) precipitated, whereby it is unnecessary to isolate the 6-substituted 2(1H)-quinoxalinone-N-oxide of the formula (II) and its alkali salt, or to dissolve them for use.

Accordingly, the reduction reaction of the present invention can be applied to a slurry system having the alkali salt of the 6-substituted 2(1H)-quinoxalinone-N-oxide of the formula (II) formed from the 4-halogeno-2-nitroacetoacetoanilide of the formula (III), precipitated, whereby the process will be highly economical from the viewpoint of the operation and apparatus. Particularly, the slurry system having the sodium salt of the 6-substituted 2(1H)-quinoxalinone-N-oxide of the formula (II), precipitated, will be more economical, since sodium hydroxide used is inexpensive.

Now, the method for acid treatment of the formed alkali salt of the 6-substituted 2(1H)-quinoxalinone of he formula (I), will be described below.

The 6-substituted 2(1H)-quinoxalinone of the formula (I) usually has a low solubility in various solvents, and accordingly, the reaction product is acidified and then subjected to filtration and washing, whereby the 6-substituted 2(1H)-quinoxalinone of the formula (I) can be obtained quantitatively.

The acid may, for example, be a mineral acid such as hydrochloric acid, sulfuric acid or nitric acid, or an organic acid such as p-toluenesulfonic acid, and it may be used as it is or in the form of an aqueous acid solution or the like.

The amount of the acid to be used, is usually an amount whereby the reaction product becomes acidic.

The temperature for the acid treatment is usually within a range of from 80° to 100° C., preferably within a range of from 90° to 100° C.

As the acid treatment method, a method is preferred wherein the reaction product is added to the acid.

When the reaction product is added to the acid, the particle sizes of precipitated crystals of the 6-substituted 2(1H)-quinoxalinone of the formula (I) will be large, whereby the filtration property will be improved, and drying will be facilitated.

If the acid is added to the reaction product, the particle sizes of the precipitated crystals of the 6-substituted 2(1H)-quinoxalinone of the formula (I) tend to be small, whereby the filtration property tends to be poor, and the drying tends to be difficult.

The 6-substituted 2(1H)-quinoxalinone of the formula (I) thus obtained, can be further purified by such a means as alkali and acid treatment, recrystallization or chromatography, as the case requires.

Further, the 6-substituted 2(1H)-quinoxalinone of the formula (I) can be readily led to 2-chloro-6-substituted quinoxaline by reacting it with a chlorinating agent such as thionyl chloride.

Further, the alkali salt of the 6-substituted 2(1H)-quinoxalinone of the formula (I) can also be readily led to 2-chloro-6-substituted quinoxaline by reacting it with a chlorinating agent such as thionyl chloride in the presence of a small amount of the 6-substituted 2(1H)-quinoxalinone of the formula (I).

According to the present invention, an inexpensive alkali metal hydrosulfide and/or alkali metal sulfide is used as a reducing agent, whereby a 6-substituted 2(1H)-quinoxalinone of the formula (II) can readily be obtained from a 6-substituted 2(1H)-quinoxalinone-N-oxide of the formula (I) at a high conversion and high selectivity.

Further, using the 4-halogeno-2-nitroacetoacetoanilide of the formula (III), the reaction mixture containing the formed alkali salt of the 6-substituted 2(1H)-quinoxalinone-N-oxide of the formula (I) can be directly subjected to the reduction reaction.

BEST MODE FOR CARRYING OUT THE INVENTION

Now, the present invention will be described in further detail with reference to Examples. However, the present invention is by no means restricted by such Examples.

EXAMPLE 1

20 g of 6-chloro-2(1H)-quinoxalinone-N-oxide, 6 g of sodium hydroxide and 200 g of water were charged into a 500 ml flask, and 60 g of a 15% sodium hydrosulfide aqueous solution was added at 80° C. over a period of 2 hours and reacted for 10 hours.

After the reaction, a small amount of insolubles were filtered off to obtain a red transparent filtrate.

To this red transparent filtrate, 300 ml of a 5% hydrochloric acid aqueous solution of 20° C. was added, whereupon fine crystals precipitated.

The precipitated crystals were collected by filtration and washed twice with water, followed by drying to obtain 17 g (yield: 92.5%) of 6-chloro-2(1H)-quinoxalinone.

The particle size of the obtained crystals was 1 μm.

EXAMPLE 2

The red transparent filtrate obtained by the same reaction as in Example 1, was gradually added to 300 ml of a 5% hydrochloric acid aqueous solution maintained at 90° C., followed by cooling to 30° C., whereby crystals having large particle sizes precipitated.

The precipitated crystals were collected by filtration and washed twice with water, followed by drying to obtain 17 g (yield: 92.5%) of 6-chloro-2(1H)-quinoxalinone.

The particle sizes of the obtained crystals were from 10 to 30 μm, whereby the filtration property was improved, and the drying speed was quick, as compared with Example 1.

EXAMPLE 3

8 g of sodium hydroxide, 50 g of water and 20 g of toluene were charged into a 500 ml flask, and 10 g of 4-chloro-2-nitroacetoacetoanilide was added at 60° C. over a period of 30 minutes and reacted for 3 hours.

To the reaction mixture slurry containing the formed sodium salt of 6-chloro-2(1H)-quinoxalinone-N-oxide, 26 g of a 15% sodium hydrosulfide aqueous solution was added at from 80° to 90° C. over a period of 2 hours and then reacted at from 80 to 90° C. for 8 hours.

After the reaction, the reaction mixture was subjected to hot filtration, and a small amount of the obtained solid was washed 3 times with water.

To the mixture of this solid and filtrate, 200 ml of a 10% hydrochloric acid aqueous solution of 20° C. was added, whereby fine crystals precipitated.

The precipitated crystals were collected by filtration and washed twice with water, followed by drying to obtain 5.7 g (yield: 80%) of 6-chloro-2(1H)-quinoxalinone.

The particle size of the obtained crystals was 1 μm.

EXAMPLE 4

The mixture of a small amount of the solid and filtrate obtained by the same reaction as in Example 3, was gradually added to 200 ml of a 10% hydrochloric acid aqueous solution maintained at 90° C., followed by cooling to 30° C., whereby crystals having large particle sizes precipitated.

The precipitated crystals were collected by filtration and washed twice with water, followed by drying to obtain 5.8 g (yield: 81%) of 6-chloro-2(1H)-quinoxalinone.

The particle sizes of the obtained crystals were from 10 to 30 μm, whereby the filtration property was improved, and the drying speed was quick, as compared with Example 3.

EXAMPLE 5

12 g of sodium hydroxide and 75 g of water were charged into a 500 ml flask, and 15 g of 4-chloro-2- nitroacetoacetoanilide was gradually added at 60° C. and reacted for 2 hours.

To a dark red reaction mixture slurry containing the formed sodium salt of 6-chloro-2(1H)-quinoxalinone-N-oxide, 22.9 g of a 15% sodium hydrosulfide aqueous solution was added at 60° C. and then reacted at 100° C. for 4 hours.

After the reaction, the reaction mixture was cooled to 20° C., followed by filtration to obtain a solid.

This solid was gradually added to 100 ml of a 10% hydrochloric acid aqueous solution maintained at 90° C., followed by cooling to 30° C., whereby orange-colored crystals having large particle sizes precipitated.

The precipitated crystals were collected by filtration and washed twice with water, followed by drying to obtain 9.0 g (yield: 85%) of 6-chloro-2(1H)-quinoxalinone.

REFERENCE EXAMPLE 1

Into a 1 liter flask, 100 g of toluene, 300 g of water and 48 g of sodium hydroxide were charged.

With stirring at 60° C., 51.2 g of 4-chloro-2-nitroacetoacetoanilide was gradually added.

After the reaction for 2 hours, the mixture was cooled to 30° C., and the precipitated sodium salt of 6-chloro-2(1H)-quinoxalinone-N-oxide was separated by filtration.

This sodium salt of 6-chloro-2(1H)-quinoxalinone-N-oxide was dissolved in water and then acidified with a 10 wt % hydrochloric acid aqueous solution, whereby the precipitated solid was collected by filtration, washed with water and dried to obtain 35 g (yield: 90%) of 6-chloro-2(1H)-quinoxalinone-N-oxide.

We claim:

1. A process for producing a 6-substituted 2(1H)-quinoxalinone of the formula (I):

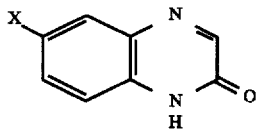

wherein X is a halogen atom, a trihalogeno-substituted $C_{1-5}$ alkyl group or a nitro group, which process comprises reacting a 6-substituted 2(1H)-quinoxalinone-N-oxide of the formula (II):

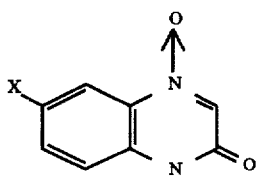

wherein X is as defined above, with an alkali metal hydrosulfide and/or an alkali metal sulfide, the reaction being carried out in the presence of an alkali, the amount of said alkali being from 1 to 20 mol of alkali per mol of 6-substituted 2(1H)-quinoxalinone-N-oxide of the formula (II).

2. The process for producing a 6-substituted 2(1H)-quinoxalinone of the formula (I) according to claim 1, wherein X is a halogen atom.

3. The process for producing a 6-substituted 2(1H)-quinoxalinone of the formula (I) according to claim 1, wherein X is a chlorine atom.

4. The process for producing a 6-substituted 2(1H)-quinoxalinone of the formula (I) according to claim 1, wherein X is a trifluoromethyl group.

5. The process for producing a 6-substituted 2(1H)-quinoxalinone of the formula (I) according to claim 1, wherein after reacting said 6-substituted 2(1H)-quinoxalinone-N-oxide of the formula (II) with an alkali metal hydrosulfide and/or an alkali metal sulfide in the presence of an alkali, the reaction product mixture is mixed with and treated with an acid.

6. The process for producing a 6-substituted 2(1H)-quinoxalinone of the formula (I) according to claim 1, wherein a 4-halogeno-2-nitroacetoacetoanilide of the formula (III):

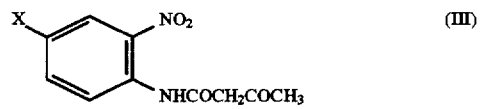

wherein X is a halogen atom, a trihalogeno-substituted $C_{1-5}$ alkyl group or a nitro group, is reacted with an alkali to obtain a reaction mixture containing an alkali salt of the 6-substituted 2(1H)-quinoxalinone-N-oxide of the formula (II), and then the reaction mixture is further reacted with an alkali metal hydrosulfide and/or an alkali metal sulfide.

7. The process for producing a 6-substituted 2(1H)-quinoxalinone of the formula (I) according to claim 1, wherein the 4-halogeno-2-nitroacetoacetoanilide of the formula (III) is reacted with an alkali to obtain a reaction product mixture containing an alkali salt of the 6-substituted 2(1H)-quinoxalinone-N-oxide of the formula (II), said process further comprising mixing and treating the reaction product mixture with an acid.

8. The process of claim 1, wherein said alkali is selected from the group consisting of lithium hydroxide, sodium hydroxide or potassium hydroxide.

9. The process of claim 1, wherein said alkali is sodium hydroxide.

10. The process of claim 1, wherein said alkali is potassium hydroxide.

11. The process of claim 5, wherein the amount of acid used is sufficient to acidify the reaction product mixture.

12. The process of claim 5, wherein said acid is a mineral acid or an organic acid.

13. The process of claim 5, wherein said acid is added to the reaction product mixture.

14. The process of claim 5, wherein the reaction product mixture is added to said acid.

15. The process of claim 6, wherein the temperature of acid treatment is in the range of from 80° to 100° C.

* * * * *